United States Patent [19]
Tanaka et al.

[11] 4,117,228
[45] Sep. 26, 1978

[54] 1,3-BENZODIOXOL DERIVATIVES

[75] Inventors: Satoru Tanaka, Higashikurume; Hideaki Watanabe, Ushiku, both of Japan

[73] Assignee: Eisai Co., Ltd., Tokyo, Japan

[21] Appl. No.: 770,039

[22] Filed: Feb. 18, 1977

Related U.S. Application Data

[62] Division of Ser. No. 684,735, May 10, 1976, Pat. No. 4,051,125, which is a division of Ser. No. 609,145, Aug. 29, 1975, Pat. No. 4,026,895, which is a division of Ser. No. 503,515, Sep. 5, 1974, Pat. No. 3,981,864.

[30] Foreign Application Priority Data

Sep. 8, 1973 [JP] Japan .................................. 48-100761
Sep. 8, 1973 [JP] Japan .................................. 48-100762

[51] Int. Cl.² ......................................... C07D 405/06
[52] U.S. Cl. ................................................ 544/377
[58] Field of Search ............................. 260/268 BC

[56] References Cited
U.S. PATENT DOCUMENTS

| | | | |
|---|---|---|---|
| 3,119,826 | 1/1964 | Regnier et al. | 260/268 BC |
| 4,010,267 | 3/1977 | Regnier et al. | 424/250 |

*Primary Examiner*—Paul M. Coughlan, Jr.
*Attorney, Agent, or Firm*—Wenderoth, Lind & Ponack

[57] ABSTRACT 1,3-Benzodioxol derivatives, the new compounds, represented by the formula:

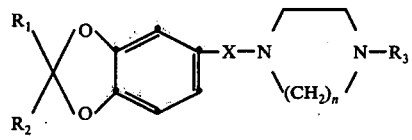

and the pharmacologically acceptable acid-addition salts thereof are provided, wherein $R_1$ and $R_2$ are lower alkyls or the both together may form a divalent alkylene, $R_3$ is a lower alkyl, phenyl, halogen-substituted phenyl or benzhydryl group, $n$ is an integer of 2 or 3, and X stands for carbonyl (CO) or methylene ($CH_2$) bridge. The compounds in which X stands for the methylene exhibit durable anti-histamic activity with low toxicity, and are useful for therapeutic purposes, while the compounds in which X stands for the carbonyl bridge are easily convertible by reduction into the former compounds.

5 Claims, No Drawings

1,3-BENZODIOXOL DERIVATIVES

This application is a division of application Ser. No. 684,735, filed May 10, 1976, now U.S. Pat. No. 4,051,125, which application is a division of application Ser. No. 609,145, filed Aug. 29, 1975, now U.S. Pat. No. 4,026,895, which application is in turn a division of application Ser. No. 503,515 filed Sept. 5, 1974, now U.S. Pat. No. 3,981,864.

This invention relates to 1,3-benzodioxol derivatives, the new compounds. More particularly, the invention relates to 1,3-benzodioxol derivatives represented by the following formula:

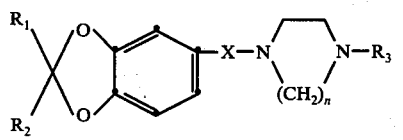

wherein $R_1$ and $R_2$ are lower alkyls or the both together in interconnection may form a divalent alkylene as a member constituting a cyclic structural moiety; $R_3$ is a lower alkyl, phenyl, halogen-substituted phenyl or benzhydryl group, $n$ is an integer of 2 or 3, and X stands for carbonyl (CO) or methylene ($CH_2$) bridge, and a process for the synthesis thereof.

It has been found that the new compounds of this invention possess anti-histamic activity and in particular 1,3-benzodioxol derivatives of the abovementioned formula (I) wherein X stands for the methylene bridge possess durable anti-histamic activity with low toxicity.

1,3-Benzodioxol derivatives of the formula (I) wherein X stands for the carbonyl may be prepared, for example, by the following schematic equation:

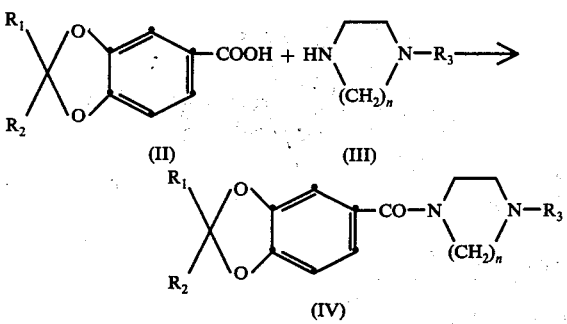

wherein $R_1$, $R_2$, $R_3$ and $n$ have the meanings same as those defined with respect to the formula (I) aforementioned. Thus, the amide compound of the formula (IV) is obtained by subjecting 2,2-di-lower-alkyl-substituted 1,3-benzodioxol-5-carboxylic acid of the formula (II) or a reactive derivative thereof to reaction with 1-substituted 1,4-diazacycloalkane of the formula (III).

Preferable class of the reactive derivatives of the starting carboxylic acid compound of the formula (II) is the corresponding acid anhydride, mixed acid anhydride, acid halide, and reactive ester thereof. The reaction can advantageously be effected in the presence of an organic solvent inert to the reaction system, such as benzene, toluene, xylene, acetone, pyridine and the like. The contemplated reaction can be performed smoothly by the addition of an acid-binding agent, such as pyridine, triethylamine, alkali carbonate, cuastic alkali and the like, to the reaction system, when the acid halide, such as acid chloride, of the carboxylic acid derivative of the formula (II) is employed. Pyridine will serve both as the acid-binding agent and also the solvent in the system.

On the other hand, 1,3-benzodioxol derivatives of the aforementioned formula (I) wherein X stands for the methylene may be obtained by the reduction of the compound of the formula (IV) in accordance with the following chemical equation:

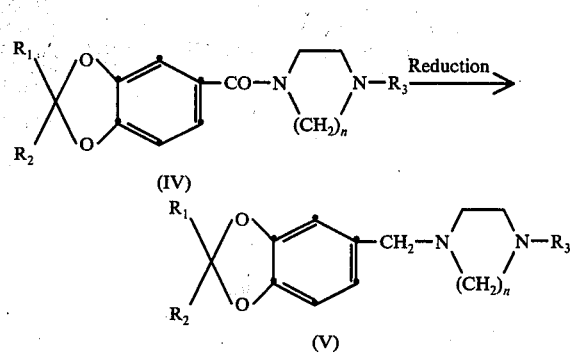

wherein $R_1$, $R_2$, $R_3$ and $n$ have the meanings same as those defined in the preceding formulae.

In carrying out the reduction procedure, there may be employed, for example, the method wherein a metal complex compounds such as lithiumaluminium hydride, sodium dihydro-bis(2-methoxy, ethoxy)aluminate and the like, and the method where a high pressure and high temperature gaseous hydrogen is employed in the presence of cupper-nickel catalyst.

As solvent for recrystallization of the resulting reduction product, there may be employed with good result any of lower alcohols, such as methanol, ethanol, propanol and a mixture of any of said alcohols with ethyl ether.

The resultant compounds (I), if desired, may be converted into the pharmacologically acceptable acid-addition salts thereof in accordance with a conventional salt-forming procedure. As the pharmacologically acceptable acids preferable for the formation of the acid-addition salts, there may be mentioned inorganic acids such as hydrochloric, sulfuric, nitric and the like acids; and organic acids such as acetic, citric, tartaric, oxalic, fumaric, maleic, methane-sulfonic and the like acids.

Anti-histamic activity presented by the compounds of the present invention was measured on the isolated organs obtained by extirpation from guinea-pig or rat by means of Magnus apparatus as follows:

EXPERIMENT 1

With 2-methyl-2-ethyl-5-(N-benzhydryl-piperazino-N'-methylene)-1,3-benzodioxol, the product of Example 9 hereinafter-mentioned Contraction of the isolated ileum under external tension caused by one gram load to be produced by applying $10^{-7}$ g/ml of histamine was retardatively controlled to an extent of % of the expected normal contraction, when the ileum has previously been treated with $10^{-5}$ g/ml of said compound. It has further been found that said retardative behavior did not disappear when the treated ileum was rinsed with Tyrode's solution more than five times in the interval of 3 minutes. The fact apparently substantiates that the compound possesses durable anti-histamic activity.

EXPERIMENT 2

With 5'-(N-methyl-homopiperazino-N'-methylene)-spirocyclohexano-1',3'-benzodioxol, the product of Example 15 hereinafter-mentioned, the following several MEC (Minimum Effective Concentrations) have been observed.

|  | MEC |
|---|---|
| Anti-histamic activity: | $10^{-5}$g/ml |
| Anti-serotonine activity: | $10^{-5}$g/ml |
| Control: Cyreheptamine | $2 \times 10^{-6}$g/ml |
| Anti-cholinergic activity: | $10^{-5}$g/ml |
| Uterine relaxation activity: | $10^{-5}$g/ml |
| Control: Isoxsuprine | $10^{-5}$g/ml |
| Intestinal organ relaxation activity: | $10^{-5}$g/ml |
| Control: Papaverine | $10^{-6}$g/ml |
| Toxicity in I. P. A. (Intraperitoneal administration): No appreciable toxic symptom appeared with 100 mg/kg. | |

As is evident from the above ovservations, the new compounds of the present invention exhibit the marked anti-histamic, anti-serotonine, anti-choline and the like activities characterized their good durability, and accordingly, they are highly useful as anti-histamic agent for the therapeutic treatments.

The following Examples serve to illustrate the invention but they are, of course, not intended to limit it thereto.

EXAMPLE 1

Synthesis of 2-methyl-2-ethyl-5-(N-benzhydryl-piperazino-N'-carbonyl)-1,3-benzodioxol 3 Grams of 2-methyl-2-ethyl-1,3-benzodioxol-5-carboxylic acid are dissolved in 4 ml of pyridine. To the resulting solution under ice-cooling with stirring, there are added 1.5 grams of thionyl chloride. After continuing the stirring for further 10 minutes, there are added 3.7 grams of N-benzhydryl-piperazine, and the mixture is heated on water bath for 30 minutes. Ice-water is added to the reaction mixture, and the acidic solution is made alkaline by neutralizing with a 5% aqueous sodium hydroxide solution. Oily substance separated out is extracted with ethyl acetate ester. The esteral extract is washed with water, dried on magnesium sulfate, and the solvent is distilled off from the dry extract. There are obtained 4.5 grams of the residue. The resulting product is in a free base which is identified by converting it into the corresponding hydrochloride as follows:

To a quatient of the residue, there are added a 10% ethanolic hydrochloric acid. The solution thus obtained is concentrated under reduced pressure to dryness. The residue is crystallized from ethanol and has a melting point of 200°–210° C. Elementary analysis of the hydrochloride having the presumable formula $C_{28}H_{30}N_2O_3 \cdot HCl$ gives the following data:

|  | C | H | N |
|---|---|---|---|
| Calculated (%): | 69.34 | 6.58 | 5.78 |
| Found (%): | 69.37 | 6.57 | 5.72 |

EXAMPLE 2

Synthesis of 2-methyl-2-ethyl-5-(N-methyl-homopiperazino-N'-carbonyl)-1,3-benzodioxol In accordance with the procedure given in the preceding Example, 2-methyl-2-ethyl-1,3-benzodioxol-5-carboxylic acid is subjected to reaction with N-methyl-homopiperazine. The product thus obtained is identified as its hydrochloride having a melting point of 218°–220° C. Elementary analysis of the hydrochloride having the presumable formula $C_{17}H_{24}N_2O_3 \cdot HCl$ gives the following data:

|  | C | H | N |
|---|---|---|---|
| Calculated (%): | 59.90 | 7.39 | 8.21 |
| Found (%): | 59.70 | 7.51 | 8.20 |

EXAMPLE 3

Synthesis of 2-cyclohexyl-spiro-5-(N-methyl-piperazino-N'-carbonyl)-1,3-benzodioxol 2-cyclohexyl-spiro-1,3-benzodioxol-5-carboxylic acid is subjected to reaction with N-methyl-piperazine in accordance with the procedure given in Example 1. The reaction product thus obtained is identified as its hydrochloride having a melting point of 260°–270° C. Elementary analysis of the hydrochloride of the product having the presumable formula $C_{18}H_{24}N_2O_3 \cdot HCl$ gives the following data:

|  | C | H | N |
|---|---|---|---|
| Calculated (%): | 61.27 | 7.14 | 7.93 |
| Found (%): | 61.24 | 7.22 | 8.03 |

EXAMPLE 4

Synthesis of 2-cyclohexyl-spiro-5-(N-benzhydryl-piperazino-N'-carbonyl)-1,3-benzodioxol 2-Cyclohexyl-spiro-1,3-benzodioxol-5-carboxylic acid is subjected to reaction with N-benzhydryl-piperazine, in accordance with the procedure given in Example 1. The purposed reaction product thus obtained is identified as its hydrochloride having a melting point of 218°–222° C. Elementary analysis of the hydrochloride of the product having the presumable formula $C_{30}H_{32}N_2O_3 \cdot HCl$ gives the following data:

|  | C | H | N |
|---|---|---|---|
| Calculated (%): | 71.34 | 6.58 | 5.54 |
| Found (%): | 71.67 | 6.62 | 5.53 |

EXAMPLE 5

Synthesis of 2,2-dimethyl-5-(N-methyl-piperazino-N'-carbonyl)-1,3-benzodioxol 2,2-Dimethyl-1,3-benzodioxol-5-carboxylic acid is subjected to reaction with N-methyl-piperazine in accordance with the procedure disclosed in Example 1. The purposed reaction product is identified as its hydrochloride having a melting point of 230°–240° C. Elementary analysis of the hydrochloride of the product having presumable formula $C_{15}H_{20}N_2O_3 \cdot HCl \cdot \frac{1}{4}H_2O$ gives the following data:

|  | C | H | N |
|---|---|---|---|
| Calculated (%): | 56.78 | 6.83 | 8.82 |

|  | -continued | | |
|---|---|---|---|
|  | C | H | N |
| Found (%): | 57.07 | 6.85 | 8.86 |

EXAMPLE 6

Synthesis of 2,2-dimethyl-5-(N-methyl-homopiperazino-N'-carbonyl)-1,3-benzodioxol 2,2-Dimethyl-1,3-benzodioxol-5-carboxylic acid is subjected to reaction with N-methyl-homopiperazine in accordance with the procedure disclosed in Example 1. The contemplated reaction product thus obtained is identified in a form of its hydrochloride having a melting point of 190°–198° C. Elementary analysis of the hydrochloride having the presumable formula $C_{16}H_{22}N_2O_3 \cdot HCl \cdot \frac{1}{2}H_2O$ gives the following data:

|  | C | H | N |
|---|---|---|---|
| Calculated (%): | 57.21 | 7.20 | 8.34 |
| Found (%): | 57.32 | 7.27 | 7.30 |

EXAMPLE 7

Synthesis of 2-methyl-2-ethyl-5-(N-methyl-piperazino-N'-carbonyl)-1,3-benzodioxol 2-Methyl-2-ethyl-1,3-benzodioxol-5-carboxylic acid is subjected to reaction with N-methyl-piperazine in accordance with the procedure disclosed in Example 1. The resulting reaction product is identified in a form of its hydrochloride having a melting point of 190°–200° C. Elementary analysis of the hydrochloride having the presumable formula $C_{16}H_{22}N_2O_3 \cdot HCl \cdot \frac{3}{4}H_2O$ gives the following data:

|  | C | H | N |
|---|---|---|---|
| Calculated (%): | 56.72 | 7.28 | 8.26 |
| Found (%): | 59.32 | 7.29 | 7.30 |

EXAMPLE 8

Synthesis of 2-cyclohexyl-spiro-5-(N-methyl-homopiperazino-N'-carbonyl)-1,3-benzodioxol 2-Cyclohexyl-spiro-1,3-benzodioxol-5-carboxylic acid is subjected to reaction with N-methyl-homopiperazine in accordance with the procedure disclosed in Example 1. The contemplated reaction product thus obtained is identified in a form of its hydrochloride having a melting point of 233°–237° C. Elementary analysis of the hydrochloride having the presumable formula $C_{19}H_{26}N_2O_3 \cdot HCl$ gives the following data:

|  | C | H | N |
|---|---|---|---|
| Calculated (%): | 62.20 | 7.41 | 7.63 |
| Found (%): | 62.04 | 7.48 | 7.82 |

EXAMPLE 9

Synthesis of 2-methyl-2-ethyl-5-(N-benzhydryl-piperazino-N'-methylene)-1,3-benzodioxol 4.0 Grams of 2-methyl-2-ethyl-5-(N-benzhydryl-piperazino)-N'-carbonyl-1,3-benzodioxol are introduced into a benzene solution containing 3 grams of sodium dihydro-bis(2-methoxy, ethoxy)aluminate. The mixture is warmed at 80° C. with stirring for 2 hours.

To the liquid reaction mixture under ice-cooling, there is added water, and the mixture is extracted with ether. The etheral extract is washed with water, dried on magnesium sulfate, and the solvent is removed by distillation under reduced pressure. A 10% ethanolic hydrochloric acid is added to the residue and the mixture is concentrated under reduced pressure to dryness. The residue is recrystallized from a mixture of ethanol and ethyl ether to obtain the hydrochloride of the purposed product with 4.1 grams of yield, and having a melting point of 219°–221° C.

Elementary analysis of the hydrochloride having the presumable formula $C_{28}H_{32}N_2O_2 \cdot 2HCl \cdot \frac{1}{2}H_2O$ gives the following data:

|  | C | H | N |
|---|---|---|---|
| Calculated (%): | 67.05 | 6.83 | 5.59 |
| Found (%): | 67.02 | 6.88 | 5.57 |

Further working Examples 10–21 are conducted in accordance with the procedure analoguous to that disclosed in the preceding Example 9. The data of the products thus obtained are listed in the following Table.

TABLE 1

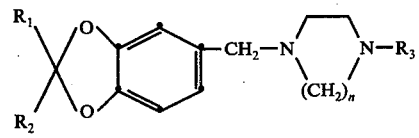

| No. of Example | $R_1$ | $R_2$ | $R_3$ | n | Formula (M.P. ° C) | Elementary Analysis Calculated (%) Found (%) | | |
|---|---|---|---|---|---|---|---|---|
|  |  |  |  |  |  | C | H | N |
| 10 | $CH_3$ | $C_2H_5$ | $CH_3$ | 3 | $C_{17}H_{26}N_2O_2 \cdot 2HCl \cdot 2/3H_2O$ (198°) | 54.40 / 54.32 | 7.90 / 8.06 | 7.46 / 7.32 |
| 11 | —$(CH_2)_5$— | | $CH_3$ | 2 | $C_{18}H_{26}N_2O_2 \cdot 2HCl$ (243–249°) | 57.60 / 57.56 | 7.51 / 7.50 | 7.46 / 7.32 |

TABLE 1-continued

| No. of Example | $R_1$ | $R_2$ | $R_3$ | n | Formula (M.P. °C) | Calculated (%) Found (%) C | H | N |
|---|---|---|---|---|---|---|---|---|
| 12 | —(CH$_2$)$_5$— | | benzhydryl (CH) | 2 | $C_{30}H_{34}N_2O_2 \cdot 2HCl \cdot \frac{1}{2} H_2O$ (225–229°) | 67.16 / 67.23 | 6.95 / 6.84 | 5.22 / 5.35 |
| 13 | CH$_3$ | CH$_3$ | CH$_3$ | 2 | $C_{15}H_{22}N_2O_2 \cdot 2HCl$ (249–251°) | 53.74 / 53.38 | 7.22 / 7.38 | 8.35 / 8.38 |
| 14 | CH$_3$ | C$_2$H$_5$ | CH$_3$ | 2 | $C_{16}H_{24}N_2O_2 \cdot 2HCl \cdot 2H_2O$ (221–225°) | 49.87 / 49.90 | 7.84 / 7.77 | 7.27 / 7.40 |
| 15 | —(CH$_2$)$_5$— | | CH$_3$ | 3 | $C_{19}H_{28}N_2O_2 \cdot 2HCl \cdot \frac{1}{2} H_2O$ (243–246°) | 57.94 / 58.12 | 7.81 / 7.85 | 7.11 / 7.27 |
| 16 | CH$_3$ | CH$_3$ | —C$_6$H$_4$—Cl | 2 | $C_{20}H_{23}N_2O_2Cl \cdot HCl \cdot \frac{1}{2} H_2O$ (217–220°) | 59.56 / 59.41 | 6.01 / 6.23 | 7.00 / 6.93 |
| 17 | CH$_3$ | C$_2$H$_5$ | —C$_6$H$_4$—Cl | 2 | $C_{21}H_{25}N_2O_2Cl \cdot 2HCl$ (208–212°) | 56.58 / 56.31 | 6.10 / 6.32 | 6.28 / 6.41 |
| 18 | —(CH$_2$)$_4$— | | CH$_3$ | 2 | $C_{17}H_{24}N_2O_2 \cdot 2HCl$ (238–242°) | 56.51 / 56.45 | 7.25 / 7.28 | 7.75 / 7.51 |
| 19 | —(CH$_2$)$_4$— | | —C$_6$H$_5$ | 2 | $C_{22}H_{26}N_2O_2 \cdot 2HCl \cdot \frac{1}{2} H_2O$ (210–213°) | 61.54 / 61.85 | 6.89 / 6.71 | 6.52 / 6.71 |
| 20 | —(CH$_2$)$_4$— | | —C$_6$H$_4$—Cl | 2 | $C_{22}H_{26}N_2O_2Cl \cdot HCl$ (213°) | 62.71 / 62.55 | 6.22 / 6.20 | 6.85 / 6.82 |
| 21 | —(CH$_2$)$_4$— | | benzhydryl (CH) | 2 | $C_{29}H_{32}N_2O_2 \cdot 2HCl$ (242–246°) | 67.83 / 67.78 | 6.67 / 6.72 | 5.46 / 5.42 |

What is claimed is:

1. A member selected from the group consisting of a compound of the formula

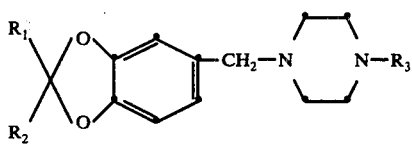

wherein $R_1$ and $R_2$ are respectively lower alkyl of 1–2 carbon atoms and $R_3$ is methyl, phenyl, chlorophenyl or benzhydryl, and a pharmacologically acceptable acid addition salt thereof.

2. A compound according to claim 1 wherein $R_1$ is methyl, $R_2$ is ethyl, and $R_3$ is benzhydryl.

3. A compound according to claim 1 wherein $R_1$, $R_2$ adn $R_3$ are methyl.

4. A compound according to claim 1 wherein $R_1$ is methyl, $R_2$ is methyl and $R_3$ is p-chlorophenyl.

5. A compound according to claim 1 wherein $R_1$ is methyl, $R_2$ is ethyl and $R_3$ is p-chlorophenyl.

* * * * *